(12) United States Patent
Khan

(10) Patent No.: US 10,267,742 B2
(45) Date of Patent: Apr. 23, 2019

(54) ANALYSIS OF COLORIMETRIC OR FLUOROMETRIC TEST ASSAYS

(71) Applicant: ELUCID MHEALTH LIMITED, Manchester (GB)

(72) Inventor: Farid Khan, Manchester (GB)

(73) Assignee: Lumophore Limited (GB)

( * ) Notice: Subject to any disclaimer, the term of this patent is extended or adjusted under 35 U.S.C. 154(b) by 605 days.

(21) Appl. No.: 14/367,187

(22) PCT Filed: Dec. 19, 2012

(86) PCT No.: PCT/GB2012/053182
§ 371 (c)(1),
(2) Date: Jun. 19, 2014

(87) PCT Pub. No.: WO2013/093454
PCT Pub. Date: Jun. 27, 2013

(65) Prior Publication Data
US 2014/0356864 A1    Dec. 4, 2014

(30) Foreign Application Priority Data

Dec. 19, 2011 (GB) .................................. 1121820.3

(51) Int. Cl.
*G01N 21/25* (2006.01)
*G01N 21/76* (2006.01)
(Continued)

(52) U.S. Cl.
CPC .......... *G01N 21/763* (2013.01); *G01N 21/25* (2013.01); *G01N 21/6428* (2013.01);
(Continued)

(58) Field of Classification Search
CPC .. G01N 21/763; G01N 21/6428; G01N 21/25; G01N 21/274; G01N 2201/0222; G01N 2201/0221
See application file for complete search history.

(56) References Cited

U.S. PATENT DOCUMENTS

2005/0203353 A1    9/2005  Ma et al.
2006/0222567 A1*  10/2006  Kloepfer ................ G01N 21/78
                                                        422/68.1
(Continued)

FOREIGN PATENT DOCUMENTS

CN       202003084 U    10/2011
WO       WO 00/20898 A2  9/1999

OTHER PUBLICATIONS

International Search Report Performed within the IPO—GB1121820.3—Completed Apr. 18, 2013.
(Continued)

*Primary Examiner* — Gailene Gabel
(74) *Attorney, Agent, or Firm* — Leydig, Voit & Mayer, Ltd.; Gerald T. Gray

(57) ABSTRACT

The present invention provides for the analysis of colorimetric or fluorometric assays by way of capturing an image of the assay on the camera (32) built into the mobile phone (30). A disposable tool (20) is provided to enable the assay to be positioned an appropriate distance from the phone camera (30). A software application on the phone (30) can then analyze the captured image to determinate a qualitative or quantitative outcome of the assay. In many examples, the test will require no modification of the phone hardware and is thus a convenient and cheap technique for analyzing an assay. In other embodiments, other disposable items such filter(s) (41, 42) and/or additional light source(s) (LED 22) may be provided.

8 Claims, 2 Drawing Sheets

(51) Int. Cl.
*G01N 21/64* (2006.01)
*G01N 21/27* (2006.01)
(52) U.S. Cl.
CPC ... *G01N 21/274* (2013.01); *G01N 2201/0221* (2013.01); *G01N 2201/0222* (2013.01)

(56) References Cited

U.S. PATENT DOCUMENTS

| | | | |
|---|---|---|---|
| 2008/0014571 A1 | 1/2008 | Teich et al. | |
| 2008/0266653 A1 | 10/2008 | Korpinen et al. | |
| 2010/0110439 A1* | 5/2010 | Gruler | G01N 21/255 356/440 |
| 2010/0254581 A1* | 10/2010 | Neeser | A61B 5/0077 382/128 |
| 2011/0009163 A1 | 1/2011 | Fletcher et al. | |
| 2012/0280144 A1* | 11/2012 | Guilfoyle | G01J 3/4406 250/458.1 |
| 2014/0154792 A1* | 6/2014 | Moynihan | G01N 21/645 435/287.2 |

OTHER PUBLICATIONS

International Search Report Performed within the EPO—PCT/GB2012/053182—Completed Mar. 6, 2013.

\* cited by examiner

Sample: Green Fluorescent Protein (GFP) at (1mg/mL-50uL)

Image with filters

Image without filters

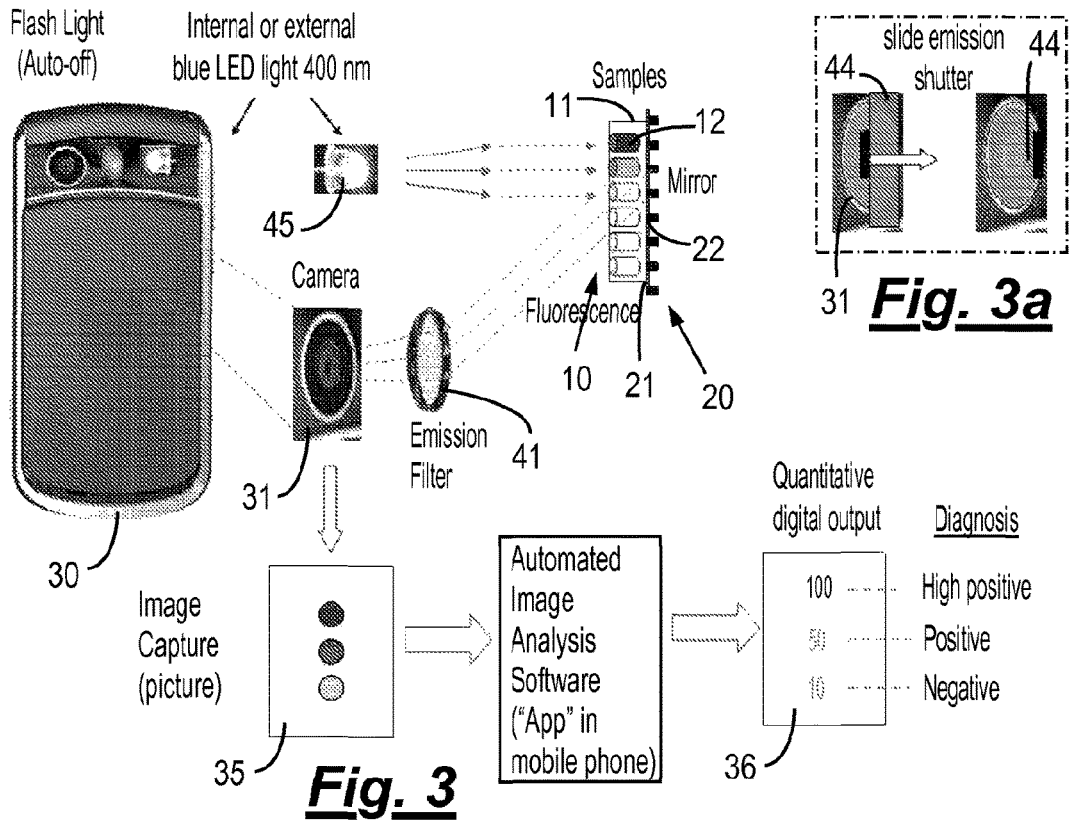
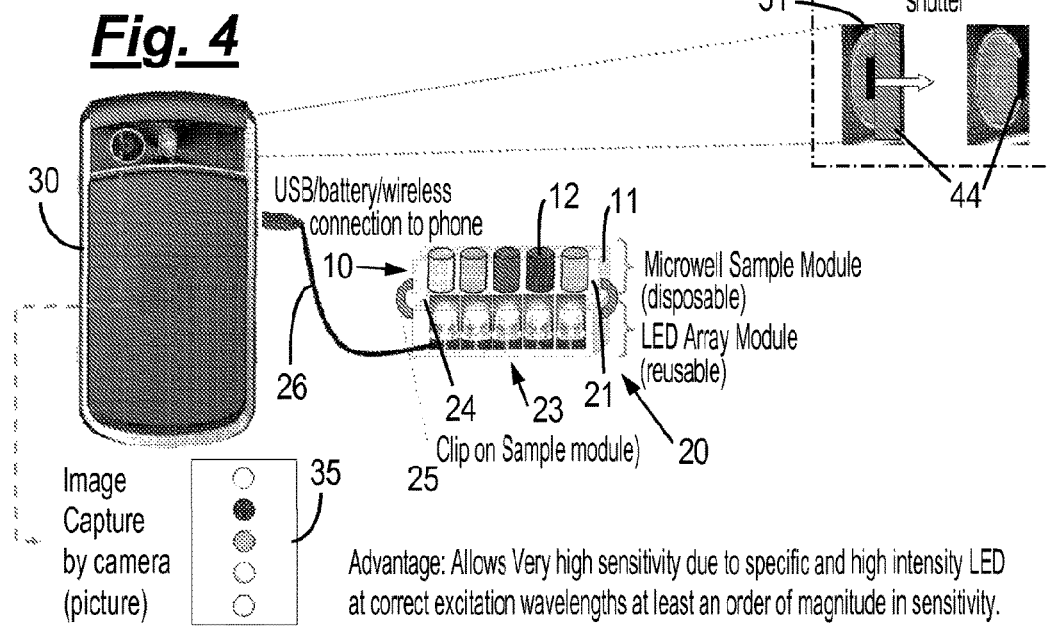

ANALYSIS OF COLORIMETRIC OR FLUOROMETRIC TEST ASSAYS

The present invention relates to the analysis of colorimetric or fluorometric test assays and in particular to a tool and method for enabling such analysis of portable assays using mobile devices.

Colorimetric or fluorometric test assays are used in many portable diagnostic tests. Typically an assay substrate is exposed to a test sample. In response to the presence of a particular component (the analyte) within the sample, suitable markers (the analytical reagent) trapped in particular positions on the substrate are able to generate colorimetric or fluorometric outputs. By analysing the colour, brightness or location of such outputs, a qualitative or quantitative outcome of the assay may be determined.

More specifically, biochemical tests or assay techniques require a sample such as blood plasma, saliva, sweat, urine, feces, hair, nails, DNA etc. which contains the target analyte that is preferentially soluble in aqueous media. Biochemical tests are usually composed of biologically derived components such as antibodies, antigens or nucleic acids which recognize and bind to the analyte that is a biomarker of a particular disease or a disease element. The biochemical test method of analysis does not require a specialized microscopist, rather it commonly employs micro-titre well detection using a microplate reader with optical detection (e.g. absorbance, fluorescence or luminescence) or a real-time PCR machine for nucleic acids. Notably, such biochemical assays often require amplification of the signal for sensitive detection to yield a quantitative, semi-quantitative or digitized result; amplification is usually achieved by using enzyme conjugates that change in colour/fluorescence/luminescence or through PCR. The specificity of the assay depends on the degree to which the analytical reagent is able to bind to its specific binding partner to the exclusion of all other substances that might be present in the sample. In addition to the need for specificity, an analytical reagent must be selected that has a sufficiently high affinity for the analyte to permit an accurate measurement. For amplification of the diagnostic signal, reagents may be labelled or themselves bound to a variety of compounds such as enzymes; fluorescent, phosphorescent, and chemiluminescent dyes; latex and magnetic particles; dye crystalites, gold, silver and selenium colloids and nanoparticles; metal chelates; coenzymes; electroactive groups; oligonucleotides, stable radicals and others. Such labels serve for the detection and quantitation of binding events by either separating free and bound labeled reagents or by designing the system in such a way that the binding event effects a change in the signal produced by the label. Thus, the design, format and output of a particular assay is also critical to its specificity and sensitivity.

Biochemical tests can be sub-divided into homogeneous and heterogeneous assays. In homogenous assays, all the assay components are exclusively in solution; these are commonly known as a 'mix and read' assays (Bock. J. L. The New Era of Automated Immunoassay Am J Clin Pathol, 113:628-646, 2000) In this case, the reagents are simply mixed together as liquids in a well with the sample and a physical measurement is taken. Homogeneous assays include immunoassays which are based on enzyme inhibition, receptor-ligand binding (antibody, antigens or aptamers) and real-time PCR assays. Heterogeneous assays, on the other hand, require a separation step. The simplest heterogenous assays are 'Immunochromatographic' tests (also known as "strip tests" and "lateral flow assays"). The most common type of biochemical tests are Enzyme-linked ImmunoSorbant Assays (ELISAs), filter-binding assays and agar plate assays (D. N. Stratis-Cullum, G. D. Griffin, J. Mobley, A. A. Vass, T. Vo-Dinh, *Anal. Chem.* 2003, 75, 275). Immunochromatographic assays are simple to operate, rapid, and commercially available, but they are less sensitive than ELISA, and give primarily yes/no results; current work focuses on improving the sensitivity and capacity of ELISAs for quantitative analysis (P. E. Andreotti, G. V. Ludwig, A. H. Peruski, J. J. Tuite, S. S. Morse, L. F. Peruski Jr., *Biotechniques* 2003, 35, 850). Moreover, although they are less expensive than many tests, they are still too costly for widespread use in developing countries, and for applications that require high-throughput analysis such as screening of blood samples. (I, V. Jani, G. Janossy, D. W. G. Brown, F. Mandy, *Lancet Infect. Dis.* 2002, 2, 243). As such, an immunoassay that is portable, rapid and simple to operate (like immunochromatographic assays), and that offers parallel, quantitative analysis and a strong, reliable analytical performance (like benchtop ELISA), will be a useful tool of detection in settings for which neither strip tests nor conventional ELISA are appropriate.

ELISA-type assays can often require multiple steps including careful washing of the surface of a microwell plate onto which the labeled reagent has been bound. Multimode detection platereaders that are capable of measuring absorbance, fluorescence or luminescence (e.g. BMG polarstar, BMG-labtech, Germany) are commonly used to read biochemical assays and yield a digitized signal. A distinct feature of a biochemical test is that the signal produced requires reference to a calibrator that mimics the characteristics of the sample medium. For qualitative assays the calibrators may consist of a negative sample with no analyte and a positive sample having the lowest concentration of the analyte that is considered detectable. Quantitative assays require additional calibrators with known analyte concentrations. Comparison of the assay response of a real sample to the assay responses produced by the calibrators makes it possible to interpret the signal strength in terms of the presence or concentration of analyte in the sample. A new molecular based assay based on the rolling circle amplification method for detection uses antibodies that are linked to oligonucleotides and forms a bridged complex between two antibodies on binding to an analyte. This has been termed as PLISA and has increased specificity and sensitivity compared to standard ELISA (Söderberg et al Direct observation of individual endogenous protein complexes in situ by proximity ligation *Nature Methods* 3, 995-1000, 2006).

Biochemical tests or assay techniques may, in theory at least, be utilized for the diagnosis of any disease condition as long as a biomarker that is predictive of such may be sampled and detected by means of an analytical reagent that binds to it and is able to generate a colorimetric or fluorometric output as a result. Clinical microscopy, on the other hand, typically relates to carrying out histological analysis (in which tissues or cells are studied under a microscope) or histopathological analysis (in which diseased tissues or cells are studied under a microscope). Such methods require the preparation of histological diagnostic samples from the blood or tissue of patients. The samples are composed of intact cells which are observed for e.g. changes in cellular morphology or the presence of intracellular parasites. Such tests are time-consuming, labour intensive and require a microscope; proper diagnosis depends on the interpretative skills of qualified laboratory technicians.

In US 20110009163 a mobile phone attachment that permits high-resolution clinical microscopy with a commercially available mobile phone is described. This document discloses a compact optical microscope mounted onto a mobile phone equipped with a 3.2 megapixel camera. The device has a magnification of up to 50× and an estimated resolution of 1.2 µm. The developers of this system have essentially created a convenient, portable clinical microscopy tool comprising a particular mobile phone and a particular high-resolution microscope that operates as an attachment to it. Whilst this is clearly of benefit in allowing certain diagnoses to be undertaken in remote locations, the expense of such a system, the requirement for highly qualified personnel and the de facto absence within the field of clinical microscopy of the sophisticated reagents utilizing the phenomena of binding and signal amplification limits its wider applicability in the diagnosis of disease.

It is therefore an object of the present invention to provide a tool and method of comparable convenience to that described in US 20110009163 which allows the diagnosis of the broadest possible range of disease conditions at point of care or in remote locations at considerable less expense and without the need for specialist personnel.

According to a first aspect of the present invention there is provided an assay analysis tool for use in the analysis of the results of a colorimetric or fluorometric assay using a mobile device incorporating a camera, the tool comprising: a mounting surface for an assay substrate; light directing means adapted to direct light onto the assay substrate when positioned on the mounting surface; and spacing means adapted to enable the mounting surface and hence the assay substrate to be positioned at an appropriate distance from the camera of the mobile device.

According to a second aspect of the present invention there is provided a method of analysing a colorimetric or fluorometric assay using a mobile device incorporating a camera, the method comprising the steps of: positioning the assay substrate at an appropriate distance from the camera of the mobile device using an assay analysis tool in accordance with the first aspect of the present invention; directing light on to the assay substrate; capturing an image of the assay substrate; and analysing the captured image to provide an indication of the outcome of the assay.

According to a third aspect of the present invention there is provided a kit of parts comprising: a colorimetric or fluorometric assay; and an assay analysis tool in accordance with the first aspect of the present invention.

The present invention thus provides for a simple, low cost, analysis of the outcomes of suitable colorimetric and fluorometric assays on commercially available mobile devices (typically mobile phones). Additionally and beneficially, the analysis can be carried out locally without requiring highly trained personnel.

The tool may be provided with retention means adapted to retain the assay substrate in a desired position on or relative to the mounting surface. The retention means may comprise adhesive means, a high friction coating or formation upon all or part of the surface. Additionally or alternatively, clips, tabs or the like may be provided to urge the assay substrate into contact with the surface.

The light directing means may comprise a mirror. The mirror may form all or part of the mounting surface. In this manner, the mirror may reflect incident light through the assay substrate.

The light directing means may alternatively comprise a substantially transparent window portion of the mounting surface. This can allow the assay substrate to be illuminated from the rear. A light source may be integrated into the tool to provide for such illumination through the window. The window may be substantially clear or may comprise a colour filter. Illumination by the light source may be substantially constant or intermittent, as required or as desired. The light source may comprise any suitable light emitting element. The light source may be a substantially white light source or may be substantially coloured. Preferably, the light source comprises one or more light emitting diodes (LEDs).

The spacing means may comprise a rigid element. The rigid element may project from the mounting surface and be adapted to connect to or rest against a mobile device at its distal end. In this manner, connecting the mobile device to the distal end or resting the mobile device against the distal end may ensure that the assay substrate is positioned at an appropriate distance from the camera of the mobile device.

Alternatively, the spacing means may comprise a flexible member. The flexible member may be adapted such that its length is equal to the appropriate distance from the camera of the mobile device to the assay substrate. In some embodiments, the flexible member may comprise a cable. The cable may be adapted to transfer power and/or data. In particular, the cable may be adapted to transfer power to the tool from the mobile device and/or data from the tool to the mobile device for analysis/interpretation. In suitable embodiments, the cable may be adapted to power and control a light source integrated into the tool.

The spacing means may additionally or alternatively comprise a pattern provided on the tool and/or the assay substrate. By analysing the size of the pattern in the image captured by the camera, an indication can be output as to whether the distance between camera and assay substrate is appropriate or not.

The tool may be supplied alongside filter means. The filter means may be adapted to be applied to any or all of: the mobile device camera, an illumination source integrated into the mobile device or the light directing means. The filter means can be adapted to be attached to the mobile device and/or tool by any suitable means. In some embodiments, the filter means may be adapted to clip onto the mobile device or tool. In other embodiments, the filter means may be adapted to adhere to the mobile device or tool. In still other embodiments, the filter means may be adapted to comprise a slide down shutter which may be positioned over the mobile device or tool.

The tool may be supplied alongside auxiliary illumination means. The auxiliary illumination means may be any suitable light source. In particular, the auxiliary illumination means may be a high power light source and/or a coloured light source. In one embodiment, the auxiliary illumination means may be a blue LED flash lamp. The auxiliary illumination means may be adapted to operate in place of or alongside an illumination source integrated into the mobile device or the light directing means.

The mobile device may be any portable electronic device incorporating a camera. Typically, the mobile device is a mobile phone. In alternative embodiments the device may be a digital camera, a tablet computer or laptop computer, a digital media player or the like.

The analysis of the captured image may be undertaken by the mobile device. The analysis may be carried out by a suitable algorithm. The algorithm may be contained in a software application running on the mobile device. The software application may be downloaded from a remote server. If so, a download address or means for directing the mobile device to the download address may be supplied alongside the tool or incorporated into the tool. Additionally or alternatively, the application may be supplied upon physical memory. The physical memory may be supplied alongside the tool or may be incorporated into the tool.

Additionally or alternatively, the mobile device may be operable to transmit the captured image and/or analysis results from the captured image to a remote device. This can allow more complex analysis to take place if necessary, provide a second opinion in respect of ambiguous results or provide an audit trail.

In order to capture an appropriate image, the mobile device may be operable to control the illumination of the assay substrate. This may be achieved by activating or deactivating an integral light source, a light source in the tool or an auxiliary light source. The activation and deactivation may be under the control of the analysis software. In particular, the mobile device may deactivate an integral light source in favour of a light source in the tool or an auxiliary light source.

The analysis might include the steps of: determining the existence of areas of colour or fluorescence in a captured image; calculating the size, shape and/or relative brightness of said areas; comparing the size, shape or relative brightness of these areas against a preset calibration; and thereby determine a qualitative or quantitative outcome of the test. The analysis might include the further step of determining the camera settings, and translating the captured image in response to variations in the camera settings from preset standard camera settings. The preset standard settings and preset calibration data may be contained in the application or may be downloaded from a remote server. Additionally or alternatively, calibration areas may be provided within the assay and/or a calibration data sheet may be provided alongside the substrate. The calibration data sheet may be adapted to be attached to the mounting surface adjacent to the assay substrate.

The indication of the outcome of the assay may take any suitable form. In particular, the indication may be provided in a digital form. The indication may comprise a visual and/or audible indication output by the phone. The visual indication may include text, as required or desired. Where the assay is quantitative, the indication may include a quantitative result.

The assay substrate may be supplied alongside the tool. The assay substrate may include directions for use and analysis. These directions may be in hard copy form or may be contained in data downloadable from a remote server. If appropriate, the directions may be incorporated into the analysis software. If required, a download address or means for directing the mobile device to the download address may be supplied alongside the tool or incorporated into the tool. Additionally or alternatively, the directions may be supplied upon physical memory. The physical memory may be supplied alongside the tool or may be incorporated into the tool.

The assay substrate may take any suitable form. In particular, the assay substrate may comprise a two dimensional solid phase slide or a three dimensional sample module. Most particularly, the assay substrate may comprise a disposable microwell plate impregnated with suitable chemical, biochemical or biological agents. The agents may be adapted to generate quantitative, relative or both quantitative and relative colorimetric, bioluminescent, fluorescent and electrical signals in response to the presence of biomarkers, bacteria, fungi, viruses, chemicals or metal ions within samples of the fluids or tissues of animate or inanimate organisms or solid, semi-solid or liquid samples of organic or inorganic materials taken from the environment.

The assay may be operable on any suitable sample which contains the target analyte that is soluble in suitable media. Examples of suitable samples include but are not limited to: blood plasma, breath, saliva, sweat, urine, feces, hair, nails, DNA. The active reagents in the assay may comprise any suitable substance, including but not limited to antibodies, antigens, nucleic acids and aptamers. For amplification of the diagnostic signal, reagents may be labeled or bound to a variety of compounds including but not limited to: enzymes; fluorescent, phosphorescent, and chemiluminescent dyes; latex and magnetic particles; dye crystalites, gold, silver and selenium colloids and nanoparticles; metal chelates; coenzymes; electroactive groups; oligonucleotides, stable radicals and others.

The assay may be a homogeneous assay or a heterogeneous assay such as an Immunochromatographic test (also known as a "strip test" or a "lateral flow assay"). In particular, the assay may take the form of an Enzyme-linked ImmunoSorbant Assay (ELISAs), filter-binding assay or agar plate assay. In some instances, the assay may be based on the rolling circle amplification method for detection, and may use antibodies that are linked to oligonucleotides and form a bridged complex between two antibodies on binding to an analyte (PLISA).

In order that the invention is more clearly understood, one embodiment will be described in greater detail below by way of example only and with reference to the accompanying drawings, in which:

FIG. 3 is a schematic diagram of the analysis of a colorimetric or fluorometric assay according to an alternative implementation of the present invention;

FIG. 3a is an expanded view of the camera of the phone of FIG. 3 illustrating the possible use of a slide down shutter;

FIG. 4 is a schematic diagram of the analysis of a colorimetric or fluorometric assay according to another alternative implementation of the present invention; and FIG. 4a is an expanded view of the camera of the phone of FIG. 4 illustrating the possible use of a slide down shutter;

The present invention provides for the analysis of colorimetric or fluorometric assays using a mobile device such as a mobile phone. Typically the assays might comprise 2D solid phase slides or 3D sample modules such as disposable microwell plates impregnated with chemical, biochemical or biological agents capable of generating quantitative, relative or both quantitative and relative colorimetric, bioluminescent, fluorescent and electrical signals in response to the presence of biomarkers, bacteria, fungi, viruses, chemicals or metal ions within samples of the fluids or tissues of animate or inanimate organisms or solid, semi-solid or liquid samples of organic or inorganic materials taken from the environment.

In its most fundamental form the invention provides for the analysis of a disposable assay substrate by way of capturing an image of the assay on the camera built into the mobile phone, a disposable tool being provided to enable the assay to be positioned an appropriate distance from the phone camera. A software application on the phone can then analyse the captured image to determinate a qualitative or quantitative outcome of the assay. In many examples, the test will require no modification of the phone hardware and is thus a convenient and cheap technique for analysing an assay. In other embodiments, other disposable items such as filter(s) and/or additional light source(s) may be provided.

Figure 1:
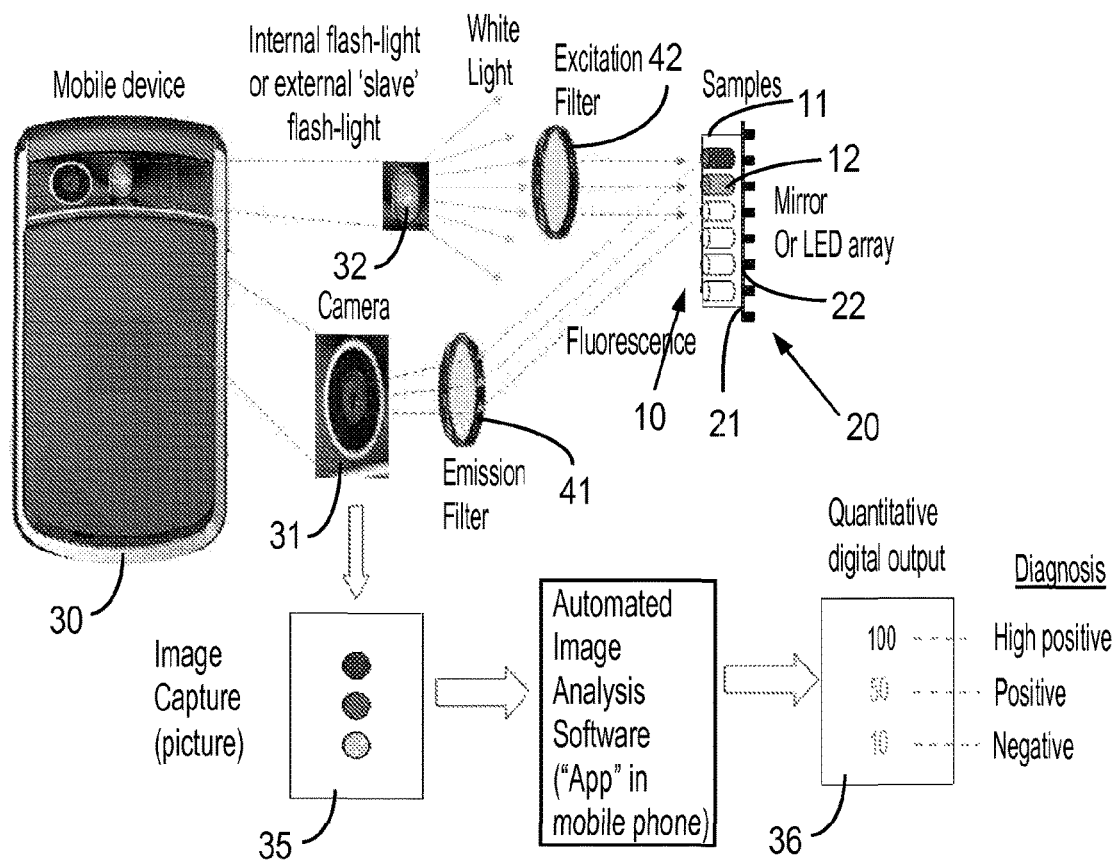
FIG. 1 is a schematic diagram of the analysis of a colorimetric or fluorometric assay according to the present invention.

Turning now to FIG. 1, a first example implementation of the invention using a mobile phone 30 with an integral camera 31 to analyse the results of an assay is illustrated. An assay substrate 10 is in the form of a plate 11 having a plurality of microwells 12. The assay substrate 10 is exposed to a test sample. In response to particular components of the sample suitable calorimetric or fluorometric markers may be trapped in one or more of the microwells 12. By analysing the colour, brightness or location of such markers, a qualitative or quantitative outcome of the assay may be determined.

The assay substrate 10 may be supplied along with an assay analysis tool 20, instructions for carrying out the assay, software for analysing a captured image of the assay and in some instances ancillary equipment 40 (typically filters and/or auxiliary illumination means). The software may typically be downloaded on to a user's phone 30. The analysis tool 20 and the optional ancillary equipment 40 may be adapted for use with particular models of phone 30.

After carrying out the assay, in order to conduct the analysis, the assay substrate 10 is mounted on the assay analysis tool 20. The tool 20 comprises a mounting surface 21, light directing means 22 and spacing means (not shown).

The mounting surface 21 is adapted to receive and retain the assay substrate 10. To achieve this, one or more clips (not shown) may be provided. Additionally or alternatively, the mounting surface 21 may be provided with an adhesive or high friction coating.

The light directing means 22 are adapted to direct light onto the assay substrate 10 when it is positioned on the mounting surface 21. In this example, the light directing means 21 comprise a mirror. This enables incident light to be reflected through the assay substrate 10.

The spacing means (not shown) are adapted to enable the mounting surface 21 and hence the assay substrate 10 to be positioned at an appropriate distance from the camera of the mobile phone 30. By way of example, the spacing means may comprise: a substantially rigid element projecting from the mounting surface and be adapted to rest against the phone 30 at its distal end, the projecting length of the rigid element equal to the appropriate distance from the camera 31 to the assay substrate 10; a flexible member with a length equal to the appropriate distance from the camera 31 to the assay substrate 10; or a pattern provided on the tool 20 and/or the assay substrate 10, the size of the pattern in the captured image providing an indication as to the distance between camera 31 and assay substrate.

After mounting the assay substrate 10 on the tool 20, the assay substrate is then positioned at a suitable distance from the camera 31. An image of the assay may then be captured using the camera 31. In some cases, the ambient light incident on the assay substrate 10 may be sufficient illumination to produce a good image for analysis. If this is not the case, the flash light 32 of the phone may be used for additional illumination. The flash light 32 may be operated under the control of the analysis software.

If necessary, an emission filter 41 for the phone camera 31 and/or an excitation filter 42 for the phone flash light 32 may be provided. These filters 41, 42 can be adapted to clip onto or adhere (temporarily) to the phone 30 over the camera 31 and flashlight 32. The filters 31, 32 are selected to pass light emitted or reflected by the active agent in the assay and light suitable for exciting the active agent in the assay respectively. Whilst the filters 41, 42 are shown in the form of clip on or stick on filters, they may alternatively be installed in the form of a slide down shutter 44, as shown in inset FIGS. 3a & 4a.

Once a suitable image is captured, it is analysed by the analysis software. The software can then display upon the screen of the phone 30 the result of the assay, whether quantitative or qualitative, as appropriate. In suitable instances, the software can further output a diagnosis on screen.

For the purposes of illustration, the analysis of the results of a sensitive quantum dot based fluorescence homogeneous assay such as that described in Chen et al. *Anal Chem*. Dual-color fluorescence and homogeneous immunoassay for the determination of human enterovirus 71. 1; 83(19):7316-22 (2011) may be considered as a representative example of the practical application of the present invention. In this document, a fluorescent immune ensemble probe comprised of conjugated water-soluble quantum dots (QDs) and an antibody complex (Ru-Ab) for the dual-color determination of human enterovirus 71 (EV71) in homogeneous solution. EV71 monoantibody was easily covalently conjugated to form a stable complex Ru-Ab, which acted both as an effective quencher of QDs fluorescence and the capture probe of virus antigen EV71. The target EV71 can break up the low fluorescent ionic ensemble by antigen-antibody combination to set free the fluorescent QDs and restore the fluorescence of QDs whereas the fluorescence intensity of Ru-Ab remains the same. Thus, the determination of EV71 by the complex Ru-Ab and QDs can be realized via the restoration of QDs fluorescence upon addition of EV71 and can be directly evaluated by the ratio of green-coloured QDs fluorescence intensity to Ru-Ab red-coloured fluorescence intensity. The green-coloured fluorescence of QDs was very sensitive to the change of EV71 concentration, and its fluorescence intensity increased with the increase of EV71 concentration between 1.8 ng/mL and 12 µg/mL. With this method, EV71 was detected at subnanogram per milliliter concentration in the presence of 160 µg/mL bovine serum albumin. By obtaining a captured image of the assay, determining the fluorescent intensity in both the red and green areas of the spectrum, a rapid and precise quantitative determination of virus presence can be provided. By analyzing the particular level of the green fluorescence one may be able to further provide a link between fluorescence and virus concentration and hence a quantitative or semiquantitative determination of virus presence. This might be expressed conveniently in terms of a scale running from e.g. 1 for the minimum detectable concentration (1.8 ng/mL) to e.g. 100 for the maximum concentration (12 µg/mL).

Figure 2A:
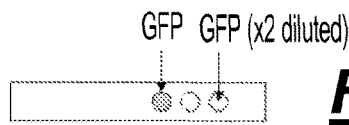
FIG. 2a is a schematic illustration of an example test assay substrate.
Figure 2B:
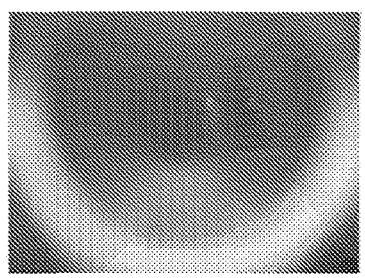
FIG. 2b is an image of the test assay substrate of FIG. 5a obtained using filters.
Figure 2C:
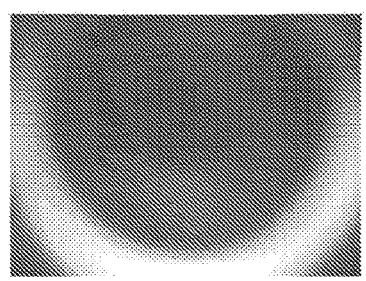
FIG. 2c is an image of the test assay substrate of FIG. 5a obtained without using filters.

In FIG. 2, an example is shown of the invention in operation using a BLACKBERRY® Smartphone 30. FIG. 2a is a schematic illustration of an example test assay substrate 10. The substrate is provided with a microwell 12a having a first concentration of green fluorescent protein (GFP) and a second microwell 12b having a 50% lower concentration of GFP. A 520 nm emission filter 41 and a 410 nm excitation filter 42 were fitted to the camera 31 and flash light 32. An example of the image captured using the filters 41, 42 is shown at FIG. 2b. For contrast an image captured without the filters 41, 42 is shown at FIG. 2b. It is therefore clear that the present invention can provide suitably clear images for automated analysis.

Turning now to FIG. 3, a further alternative implementation of the invention is shown. In this implementation, an auxiliary light 45 is provided. This can supplement or act in place of the flash light 32. If the auxiliary light is acting in place of the flash light 32, the analysis software may be operable to activate the auxiliary light and switch off the flash light 32 when appropriate.

The auxiliary light shown is in the form of a blue LED. Equally, the skilled man will appreciate that LED's of other colours can be used for the specific excitation of fluorochromes (e.g. green LED's for rhodamine or DsRed or red LED's for cyanine dyes or APC). In addition, in the above examples, for bioluminescent assays which generate their own light, only the emission filter 41 is required.

Turning now to FIG. 4, a further implementation of the invention is shown. In this implementation, the analysis tool 20 is provided with an LED array 23, which is operable to illuminate the assay substrate 10 through a substantially transparent window 24 in the mounting surface 21. The analysis tool 20 is also provided with clips 25 for retaining the assay substrate 10 on mounting surface 21.

In addition to the above, the analysis tool 20 is provided with a USB cable 26. The cable 26 allows the transfer of power and/or data between the phone 30 and the tool 20. The cable 26 may also act as a spacing means. In this context, the length of the cable 26 is selected to be substantially equal to the appropriate distance between the camera 31 and the assay substrate 10.

In use, similarly to the previous implementation, the LED array can be activated to illuminate the substrate 10 in addition to or in place of the flash lamp 32. In particular, the phone 30 may control the period and intensity of the illumination provided by the LED array. In some cases, the tool 20 may be provided with a memory unit (not shown) that contains analysis software for download to the phone 30 and directions for carrying out the assay.

Whilst the implementation above incorporates a cable, it is also possible for a wireless connection to be made between the tool 20 and phone 30. In such cases, the tool 20 is preferably provided with an internal power source such as a rechargeable battery.

It is of course to be understood that the invention is not to be restricted to the details of the above embodiment, which is described by way of example only.

The invention claimed is:

1. An assay analysis tool for use with a mobile device incorporating a camera in the analysis of a colorimetric or fluorometric assay using said mobile device incorporating the camera, the tool comprising:
   a mounting surface for an assay substrate;
   light directing means adapted to direct light onto the assay substrate when positioned on the mounting surface; and
   spacing means comprising a flexible member configured to have a length equal to an appropriate operable distance from the camera of the mobile device to the assay substrate,
   the flexible member being adapted to connect the assay analysis tool to the mobile device and adapted to enable the mounting surface and hence the assay substrate to be positioned at the appropriate operable distance from the camera of the mobile device when the flexible member connects the assay analysis tool to the mobile device,
   wherein the operable distance is configured such that when the mounting surface is positioned at the operable distance from the camera of the mobile device, the camera of the mobile device is able to capture an image of the mounting surface and hence the assay substrate, and
   wherein the flexible member is a cable adapted to transfer power and/or data to the assay analysis tool from the mobile device and/or data from the assay analysis tool to the mobile device for analysis.

2. The assay analysis tool according to claim 1 wherein the tool is provided with retention means on the mounting surface, the retention means adapted to retain the assay substrate in a position on or relative to the mounting surface and wherein the retention means comprise any one or more of: adhesive means; or clips or tabs provided to urge the assay substrate into contact with the surface.

3. The assay analysis tool according to claim 1 wherein the light directing means comprises a mirror.

4. The analysis tool according to claim 1 wherein the light directing means comprises a substantially transparent window portion of the mounting surface.

5. The assay analysis tool according to claim 1 comprising a physical memory, wherein an analysis software application is stored in the physical memory.

6. A method of analysing a colorimetric or fluorometric assay using a mobile device incorporating a camera, the method comprising the steps of:
   positioning an assay substrate at the appropriate operable distance from the camera of the mobile device using an assay analysis tool in accordance with claim 1; directing light on to the assay substrate; capturing an image of the assay substrate; analysing the captured image and providing an indication of an outcome of the analysis to a user based on the analysis of the captured image.

7. The method as claimed in claim 6 wherein the analysis of the captured image is carried out by an algorithm contained in a software application running on the mobile device.

8. The method as claimed in claim 6, further including controlling the illumination of the assay substrate by activating or deactivating an integral light source in the mobile device, a light source in the tool or an auxiliary light source.

* * * * *